United States Patent
Müller et al.

(10) Patent No.: US 11,213,491 B2
(45) Date of Patent: Jan. 4, 2022

(54) FILM-LIKE FORM OF ADMINISTRATION FOR THE TRANSMUCOSAL DELIVERY OF ANTIDIABETIC PEPTIDES

(71) Applicant: LTS Lohmann Therapie-Systeme AG, Andernach (DE)

(72) Inventors: Markus Müller, Troisdorf (DE); Claudia Maria Hammes, Andernach (DE); Christoph Schmitz, Rheinbrohl (DE); Michael Linn, Waldböckelheim (DE); Mohammad Sameti, Bonn (DE); Peter Klaffenbach, Niederkassel (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 16/094,933

(22) PCT Filed: Apr. 20, 2017

(86) PCT No.: PCT/EP2017/059379
§ 371 (c)(1),
(2) Date: Oct. 19, 2018

(87) PCT Pub. No.: WO2017/186563
PCT Pub. Date: Nov. 2, 2017

(65) Prior Publication Data
US 2019/0125692 A1    May 2, 2019

(30) Foreign Application Priority Data
Apr. 26, 2016 (EP) .................................. 16167053

(51) Int. Cl.
*A61K 9/70* (2006.01)
*A61K 38/28* (2006.01)
(Continued)

(52) U.S. Cl.
CPC ............ *A61K 9/7007* (2013.01); *A61K 9/006* (2013.01); *A61K 38/26* (2013.01); *A61K 38/28* (2013.01); *A61K 47/38* (2013.01); *A61P 3/10* (2018.01)

(58) Field of Classification Search
None
See application file for complete search history.

(56) References Cited

U.S. PATENT DOCUMENTS

2006/0034927 A1* 2/2006 Casadevall .......... A61K 9/1635
424/472

FOREIGN PATENT DOCUMENTS

| WO | 98/17251 A1 | 4/1998 |
| WO | 2009/048945 A1 | 4/2009 |

(Continued)

OTHER PUBLICATIONS

Singh et al., "Oral insulin delivery with various grades of HPMC on non-diabetic rats", Trends in Medical Research 6(1): 1-13, 2011, pp. 1-13 (Year: 2011).*

(Continued)

*Primary Examiner* — Kyung S Chang
(74) *Attorney, Agent, or Firm* — ProPat, LLC; Cathy R. Moore

(57) ABSTRACT

The invention relates to film-like forms of administration for the transmucosal delivery of antidiabetic peptides via the oral mucosa and to processes for the production thereof. Antidiabetic peptides refers to peptides which are an active compound for the treatment of diabetes mellitus, and includes insulins, insulin analogs, incretins and incretin mimetics.

26 Claims, 5 Drawing Sheets

(51) Int. Cl.
*A61K 47/38* (2006.01)
*A61P 3/10* (2006.01)
*A61P 9/00* (2006.01)
*A61K 9/00* (2006.01)
*A61K 38/26* (2006.01)

(56) References Cited

FOREIGN PATENT DOCUMENTS

| | | |
|---|---|---|
| WO | 2011/156711 A1 | 12/2011 |
| WO | 2012/104834 A1 | 8/2012 |

OTHER PUBLICATIONS

International Search Report of Publication WO 2017/186563 A1.
Heinemann, L. and Jacques, Y., "Oral Insulin and Buccal Insulin: A Critical Reappraisal," Journal of Diabetes Science and Technology 3, (2009) pp. 568-584.

* cited by examiner

FILM-LIKE FORM OF ADMINISTRATION FOR THE TRANSMUCOSAL DELIVERY OF ANTIDIABETIC PEPTIDES

CROSS-REFERENCE TO RELATED APPLICATIONS

This application is being filed under 35 U.S.C. § 371 as a National Stage Application of pending International Application No. PCT/EP2017/059379 filed Apr. 20, 2017, which claims priority to the following parent application: European Patent Application No. 16167053A filed Apr. 26, 2016. Both International Application No. PCT/EP2017/059379 and European Patent Application No. 16167053.4 are hereby incorporated by reference herein in their entirety.

FIELD OF THE INVENTION

The present invention relates to film-like dosage forms, more particularly film-like dosage forms for the delivery of an antidiabetic peptide via a mucous membrane.

BACKGROUND OF THE INVENTION

Diabetes (diabetes mellitus) is a metabolic disease characterized by chronically elevated blood sugar values. Diabetes is caused by a deficiency of the hormone insulin (type 1 diabetes) or by reduced sensitivity of the cells to the action of insulin (type 2 diabetes).

Insulin is important for controlling the sugar concentration of the blood (blood glucose level) and is the only hormone in the body that can reduce the glucose level. In diabetes patients, chronically elevated blood sugar causes severe damage to the retina (diabetic retinopathy), sensory impairment of the nerves (neuropathy), and ketoacidosis (excess acidity due to deficient glucose utilization). However, an excessively low blood glucose level (hypoglycemia) can also cause unconsciousness (diabetic shock). For the patient's health, therefore, it is extremely important to maintain a balanced blood glucose level. Insulin can be administered for this purpose.

Because orally-administered insulin is rapidly degraded by proteolytic enzymes in the digestive tract, insulin, as well as insulin analogs and other antidiabetic peptides, is/or ordinarily administered to patients with diabetes mellitus by injection. However, this administration route is perceived by many patients as causing severe impairment of their quality of life, not least because of discomfort and/or anxiety concerning the pain accompanying injection or awkwardness due to the skin exposure required for injection.

Despite the obstacles posed by problems connected with oral administration of insulin, efforts have been made to develop oral insulin dosage forms. The review article by L. Heinemann and Y. Jaques (Heinemann, L. and Jaques, Y. (2009) *Oral Insulin and Buccal Insulin: A Critical Reappraisal.* Journal of Diabetes Science and Technology 3, pp. 568-584) provides an overview of these efforts.

In general, film-like dosage forms, by means of which insulin can be administered via the oral mucosa, are also suitable for oral delivery of the hormone. For example, WO 2012/104834 A1 discloses film-like dosage forms adhering to the mucosa that comprise a first polymer composition containing water-soluble polymers that allow the active compound to be dissolved and released within 20 minutes or less, a second polymer composition comprising hydrophilic bioadhesive polymers that allow continuous release of the active compound over a period of approximately 1 hour to approximately 20 hours, and insulin or an insulin analog as an active compound, wherein the dosage form is not thicker than 0.5 mm. Film-like dosage forms specifically described in this document were capable, at least in in vitro studies with a buccal cell model, of releasing insulin. In vivo studies, however, have not been published.

The published patent application WO 2009/048945 A1 discloses film-like preparations for the systemic delivery of insulin that can adhere to a mucous membrane. Depending on their excipients, the films are designed to dissolve or release the insulin within a period of less than 30 seconds to half an hour. The preparations contain human insulin, a zinc chelator, and a disintegrant. In the case of film-like preparations that are multilayer films, the insulin on the one hand and the zinc chelator and/or the disintegrant on the other are in separate layers, so that the active compound is stored separately from the above-mentioned excipients in order to improve the shelf life of the active compound.

The international patent application published under no. WO 98/17251 A1 relates to film-like carriers for the delivery of pharmaceutically active compounds to the surfaces of mucous membranes. These preparations are designed to be suitable for delivery of multiple active compounds, including insulin.

SUMMARY OF ADVANTAGEOUS EMBODIMENTS OF THE INVENTION

Against the backdrop of the prior art mentioned above, the object of the present invention was to provide a film-like dosage form by means of which antidiabetic peptides can be delivered via a mucous membrane of the oral cavity, wherein the residence time of the preparation on the oral mucosa is to be at least 30 minutes to one hour or even longer in order to allow a therapeutically effective amount of the antidiabetic peptide to be delivered via the oral mucosa into the bloodstream of a patient during this period. In this context, it was to be taken into account that application of the film-like dosage form to the oral mucosa was not to produce a sensation in the mouth that was unacceptable to the user. At the same time, it was to be possible to produce the dosage form continuously in order to allow production that is as efficient as possible and therefore economical.

Surprisingly, the object is achieved by means of a film-like dosage form comprising at least one active-compound-containing layer in which an antidiabetic peptide is contained as the active compound in a matrix based on at least two hydroxypropylmethylcelluloses of different viscosities.

According to a first aspect, the invention relates to a film-like dosage form for the delivery of at least one antidiabetic peptide via an oral mucosa.

According to a second aspect, the invention relates to a method for the production of a film-like dosage form for the delivery of at least one antidiabetic peptide via an oral mucosa.

According to a third aspect, the invention relates to the use of a film-like dosage form for the delivery of at least one antidiabetic peptide via an oral mucosa.

According to a further aspect, the invention comprises a method for the delivery of at least one antidiabetic peptide via the oral mucosa.

According to another further aspect, the invention comprises methods for the treatment of patients who require delivery of an antidiabetic peptide.

DETAILED DESCRIPTION OF ADVANTAGEOUS EMBODIMENTS OF THE INVENTION

Figure 1:
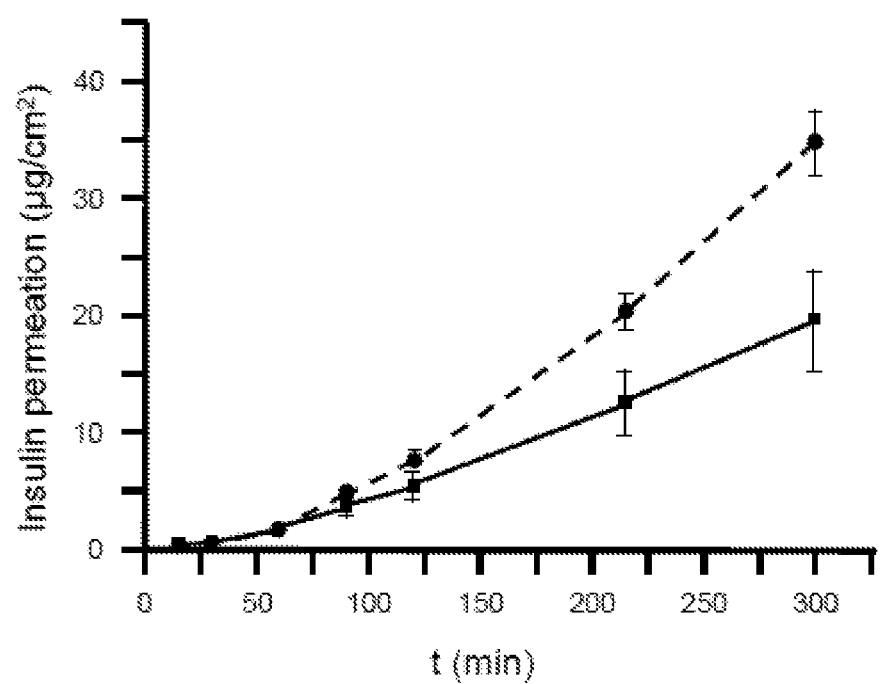
FIG. 1 shows a diagram illustrating the permeation of insulin or an insulin analog from two different film-like dosage forms in an in vitro permeation assay.

The film-like dosage form according to the first aspect comprises at least one active-compound-containing layer that includes at least one antidiabetic peptide as an active compound and, on proper application of the dosage form, comes into contact with the oral mucosa in order to release the compound it contains via the oral mucosa.

The at least one active-compound-containing layer comprises at least one antidiabetic peptide. On application of the film-like dosage form, the at least one active-compound-containing layer comes into contact with the oral mucosa and adheres thereto. The antidiabetic peptide contained in the at least one active-compound-containing layer is released from the at least one active-compound-containing layer via the oral mucosa into the bloodstream of the user.

The term "antidiabetic peptide" within the meaning of the present disclosure refers to peptides that are active as an antidiabetic, i.e. as an active compound for the treatment of diabetes mellitus. The term "antidiabetic peptide" includes insulins and insulin analogs, but also incretins and incretin mimetics.

The insulin is preferably human insulin, but porcine insulin or bovine insulin can also be used. The insulin analogs include short- and rapid-acting insulin analogs such as insulin aspart, insulin lispro, and insulin glulisine, but also longer-acting insulin analogs such as insulin detemir, insulin glargine, insulin degludec, and isophane insulin.

Insulin is a proteohormone of vital importance to all mammals that is produced in the beta cells of the pancreas. Insulin is composed of two peptide chains, the A chain with 21 amino acids and the B chain with 30 amino acids, which are covalently bonded to one another by two intermolecular disulfide bonds (Cys-A7 to Cys-B7 and Cys-A20 to Cys-B19). A third intramolecular disulfide bond binds the cysteine residues of positions 6 and 11 of the A chain.

Insulin is naturally synthesized as preproinsulin. Preproinsulin is a polypeptide molecule with 110 amino acids composed of a signal sequence 24 amino acids long, 2 amino acid residues, a B chain 30 amino acids long attached thereto, and a subsequent C peptide 31 amino acids in length, followed by two further amino acid residues and the A chain with 21 amino acids.

The preproinsulin is folded by the formation of three disulfide bonds, two between the A and B peptide, and one within the A peptide. The signal sequence and the C peptide are cleaved from the folded prepropeptide. The signal sequence is split by penetration of the preproinsulin through the membrane of the ER, giving rise to the proinsulin. The proinsulin is absorbed in the Golgi apparatus and stored there. When needed, the C chain is cleaved by specific proteases so that the resulting insulin acquires its final structure.

Porcine insulin is a purified, natural, antidiabetically-acting substance from the porcine pancreas. It has the same structure as human insulin, with the exception of position B30 of the B chain, where it has an alanine instead of a threonine.

Bovine insulin ($C_{254}H_{377}N_{65}O_{75}S_6$, $M_r$=5734 g/mol) is a purified, natural, antidiabetically-acting substance from the bovine pancreas. Bovine insulin differs from human insulin in three amino acids.

The primary structure of insulin aspart ($C_{256}H_{381}N_{65}O_{79}S_6$, $M_r$=5825.8 g/mol) is identical to the primary structure of human insulin, with the exception of asparaginic acid (=aspartic acid, hence "aspart") instead of proline at position 28 of the B chain. Replacement of the amino acid leads after subcutaneous delivery to better absorption in the blood and more rapid elimination.

Insulin lispro ($C_{257}H_{383}N_{65}O_{77}S_6$, $M_r$=5808 g/mol) has an identical primary structure to that of human insulin, with the exception of the amino acids, which are exchanged for one another at positions 28 and 29 of the B chain.

The primary structure of insulin glulisine ($C_{258}H_{384}N_{64}O_{78}S_6$, $M_r$=5823 g/mol) is identical to the primary structure of human insulin, with the following exceptions:

glutamic acid instead of lysine at position 29 of the B chain;

lysine instead of asparagine at position 3 of the B chain.

Insulin detemir ($C_{267}H_{402}O_{76}N_{64}S_6$, $M_r$=5916.9 g/mol) has an identical primary sequence to that of human insulin with the exception of the removed threonine at position B30 of the B chain and a molecule of myristic acid added to the lysine at position B29.

Insulin glargine ($C_{267}H_{404}N_{72}O_{78}S_6$, $M_r$=6063 g/mol) has the same primary structure as human insulin, with the following exceptions:

A chain: glycine instead of asparagine at position 21;

B chain: additionally, two arginines at positions 31 and 32.

Insulin degludec has essentially the same structure as human insulin, with the following exceptions:

the last amino acid of the B chain (threonine B30) is removed;

a glutamic acid and a 16-C fatty acid are attached to the lysine B29.

Isophane insulins (=NPH insulins) are insulins complexed with protamine sulfate or another suitable protamine. Protamines are basic peptides obtained by extraction from the sperm or eggs of fish (usually salmon or herrings). Isophane insulin has a later onset and a longer duration of action than conventional insulin and is classified as an intermediate-acting insulin.

The incretins include the gastrointestinal hormones that control the food-dependent secretion of insulin from the beta cells of the pancreas. The incretins include glucagon-like peptide 1 (GLP-1) and glucose-dependent insulinotropic peptide (GIP).

Glucagon-like peptide 1 is a polypeptide the amino acid sequence of which is determined by the proglucagon gene. Glucagon-like peptide can be present in two different biologically active forms, GLP-1-(7-37), with a primary structure of 30 amino acids, and GLP-1-(7-36), with a primary structure of 31 amino acids. In addition to other actions, glucagon-like peptide 1 stimulates insulin synthesis in the pancreas, reduces the glucagon level, slows gastric emptying, and suppresses feelings of hunger and thirst.

Glucose-dependent insulinotropic peptide is actually produced in the K cells of the duodenum and jejunum. It is a polypeptide with a primary structure composed of 42 amino acids. GIP promotes the release of insulin from the pancreatic B cells. It inhibits gastric motility and gastric juice secretion.

Incretin mimetics are antihyperglycemic and antihypertensive active compounds whose action mimics that of the body's own incretins. Incretin mimetics are also referred to as GLP-1 agonists, GLP-1 analogs, or GLP-1 receptor agonists. The incretin mimetics suitable for transmucosal delivery include exenatide, liraglutide, and lixisenatide.

Exenatide is a synthetic peptide composed of 39 amino acids. The substance is originally derived from the poison of the Gila monster (*Heloderma suspectum*). The natural peptide is referred to as exendin-4. Exenatide is related to the incretin glucagon-like peptide 1 (GLP-1) and has a sequence homology of 53%. Exenatide has a substantially longer half-life and duration of action than GLP-1, as it is not degraded by dipeptidyl peptidase 4 (DPP-4).

Liraglutide or $\gamma$-L-glutamoyl(N-$\alpha$-hexadecanoyl)-Lys$^{26}$, Arg$^{34}$-GLP-1(7-37) is a branched-chain peptide. It is an analog of the incretin GLP-1. Its sequence homology is 97%. Lys 34 was replaced by Arg, and a C16 fatty acid was attached to Lys 26 via a Glu spacer. These modifications allowed the half-life of GLP-1 (2 minutes) to be extended to 13 hours.

Lixisenatide is a peptide composed of 44 amino acids and a GLP-1 analog that like exenatide, was developed based on exendin-4. Lixisenatide has a longer half-life and a higher binding affinity that the natural substrate GLP-1. However, its half-life is shorter than that of liraglutide.

According to an additional and/or alternative embodiment, the at least one antidiabetic peptide is contained in the active-compound-containing layer in an amount of at least 5 wt %, more particularly at least 5.6 wt %, preferably at least 10 wt %, particularly preferably at least 12 wt %, and most particularly preferably at least 15 wt %, based on the total weight of the antidiabetic-peptide-containing layer. The antidiabetic peptide is preferably contained in the active-compound-containing layer in an amount of not more than 20 wt %, particularly preferably not more than 16 wt %, based on the total weight of the antidiabetic-peptide-containing layer. According to an additional and/or alternative embodiment, the at least one antidiabetic peptide is contained in the active-compound-containing layer in an amount of approximately 20 wt %, based on the total weight of the antidiabetic-peptide-containing layer.

The at least one active-compound-containing layer comprises a mixture of at least two hydroxypropylmethylcelluloses, a first hydroxypropylmethylcellulose and a second hydroxypropylmethylcellulose, which comprises at least one antidiabetic peptide. According to an additional and/or alternative embodiment, the at least one active-compound-containing layer comprises three hydroxypropylmethylcelluloses, a first hydroxypropylmethylcellulose, a second hydroxypropylmethylcellulose, and a third hydroxypropylmethylcellulose. The various hydroxypropylmethylcelluloses differ from one another in viscosity.

According to an additional and/or alternative embodiment, the first hydroxypropylmethylcellulose is a hydroxypropylmethylcellulose of high viscosity. A hydroxypropylmethylcellulose of high viscosity is understood to refer to a hydroxypropylmethylcellulose having a Brookfield viscosity in the range of approximately 3,000 mPa·s to approximately 5,600 mPa·s, measured with a 2% solution in water at a temperature of 20° C. on a Brookfield LV viscometer. Such hydroxypropylmethylcelluloses are also referred to as HPMC 4000.

According to an additional and/or alternative embodiment, the second hydroxypropylmethylcellulose is a hydroxypropylmethylcellulose of medium viscosity. A hydroxypropylmethylcellulose of medium viscosity is understood to refer to a hydroxypropylmethylcellulose having a Brookfield viscosity in the range of approximately 75 mPa·s to approximately 140 mPa·s, measured with a 2% solution in water at a temperature of 20° C. on a Brookfield LV viscometer. Such hydroxypropylmethylcelluloses are also referred to as HPMC 100.

According to an additional and/or alternative embodiment, the third hydroxypropylmethylcellulose is a hydroxypropylmethylcellulose of low viscosity. An HPMC with low viscosity is understood to refer to a hydroxypropylmethylcellulose with a Brookfield viscosity in the range of approximately 3 mPa·s, measured with a 2% solution in water at a temperature of 20° C. on a Brookfield LV viscometer. Such hydroxypropylmethylcelluloses are also referred to as HPMC 3.

According to an additional and/or alternative embodiment, the different hydroxypropylmethylcelluloses are present in a ratio of 1:6 to 10:0 to 6 (first HPMC:second HPMC:third HPMC). In a particular embodiment, the ratio of the first HPMC to the second HPMC is 1:9. According to other embodiments, the ratio of the first HPMC to the second HPMC to the third HPMC is 1:6.46 to 6.52:4.07 to 5.18. According to another embodiment, the ratio of the first HPMC to the second HPMC to the third HPMC is approximately 1:7.31:4.5.

The combination of the various hydroxypropylmethylcelluloses of different densities, more particularly in the above-mentioned ratios, results in a flexible film that adheres to the oral mucosa and does not cause an unpleasant foreign body sensation.

According to an additional and/or alternative embodiment, the mixture of various hydroxypropylmethylcelluloses, based in each case on the total weight of the active-compound-containing layer, is contained in an amount of at least 49 wt %, preferably at least 55 wt %, particularly preferably at least 58 wt %, and most particularly preferably at least 60 wt % in the at least one active-compound-containing layer. The mixture of various hydroxypropylmethylcelluloses is contained in an amount of not more than 74 wt %, preferably not more than 65 wt %, particularly preferably not more than 62 wt %, and most particularly preferably not more than 61 wt % in the at least one active-compound-containing layer. According to an additional and/or alternative embodiment, the mixture of various hydroxypropylmethylcelluloses is contained in an amount of approximately 51 wt % in the at least one active-compound-containing layer.

According to an additional and/or alternative embodiment, the at least one active-compound-containing layer comprises at least one plasticizer. The at least one plasticizer increases the flexibility of the film-like dosage form so that the dosage form can more easily conform to the surface of the oral mucosa and thus does not cause the unpleasant sensation of a foreign body.

The at least one plasticizer can be selected from the group of plasticizers comprising medium-chain triglycerides, glycerol, and citric acid esters, for example triethyl citrate. Medium-chain triglycerides are triglycerides comprising medium-chain fatty acid residues. Medium-chain fatty acid residues have a carbon chain with a length of 6 to 12 carbon atoms.

According to an additional and/or alternative embodiment, the at least one plasticizer or the plasticizers is/are contained in an amount of at least 4 wt %, preferably at least 5 wt %, particularly preferably at least 6 wt %, and most particularly preferably at least 9 wt % in the at least one active-compound-containing layer. The at least one plasticizer or the plasticizers is/are preferably contained in the at least one active-compound-containing layer in an amount of not more than 20 wt %, particularly preferably not more than 16.5 wt %, and most particularly preferably not more than 11 wt %. According to an additional and/or alternative embodiment, the at least one plasticizer or the plasticizers is/are contained in an amount of approximately 16 wt % in the at least one active-compound-containing layer.

According to an additional and/or alternative embodiment, the at least one active-compound-containing layer comprises at least one enhancer. The at least one enhancer improves the permeability of the active compound through the oral mucosa.

The at least one enhancer can be selected from the group comprising β-cyclodextrin, polyoxyethylene (23) lauryl ether, isopropyl myristate, soy lecithin, trehalose and glycerol, linoleic acid, oleic acid, octyldodecanol, polyethylene glycol and bile salts.

The at least one enhancer or the total enhancers can be contained in the active-compound-containing layer in an amount of at least 1 wt %, preferably at least 1.5 wt %, particularly preferably at least 4 wt %, and most particularly preferably at least 5 wt %. The at least one enhancer or the total enhancers is/are contained in the active-compound-containing layer in an amount of not more than 22 wt %, preferably in an amount of not more than 18 wt %, particularly preferably not more than 16 wt %. According to an additional and/or alternative embodiment, the at least one enhancer or the total enhancers is/are contained in an amount of approximately 16 wt % in the at least one active-compound-containing layer.

According to an additional and/or alternative embodiment, the at least one active-compound-containing layer comprises at least one stabilizer. The at least one stabilizer improves the stability of the active compound in the active-compound-containing layer, more particularly during storage of the film-like preparation, and thus increases the shelf life.

The at least one stabilizer can be selected from the group comprising β-cyclodextrin, disodium edetate, poloxamer 188 and trehalose.

The at least one stabilizer or the total stabilizers can be contained in the active-compound-containing layer in an amount of at least 0.1 wt %, preferably at least 1.4 wt %, particularly preferably at least 3.5 wt %. The at least one stabilizer or the total stabilizers is/are contained in an amount of not more than 23 wt %, preferably not more than 16 wt %, particularly preferably not more than 11 wt %, most particularly preferably not more than 8 wt %.

According to an additional and/or alternative embodiment, the stabilizer or the total stabilizers is/are contained in an amount of 2.5 wt % in the at least one active-compound-containing layer.

According to an additional and/or alternative embodiment, the at least one active-compound-containing layer comprises at least one preservative. The preservative improves the shelf life of the film-like preparation, more particularly during storage.

The at least one preservative can be selected from the group comprising methyl-4-benzoate.

The at least one preservative is contained in an amount of approximately 0.1 wt %.

According to an additional and/or alternative embodiment, the at least one active-compound-containing layer comprises at least one dye.

The dye can be selected from the group comprising titanium dioxide and iron oxide.

The dye is preferably contained in an amount of at least 0.1, preferably at least 0.5 wt %, particularly preferably at least 1 wt %, and preferably not more than 2 wt %. According to an additional and/or alternative embodiment, the dye is contained in an amount of approximately 0.5 wt % in the at least one active-compound-containing layer.

According to additional and/or alternative embodiments, the at least one active-compound-containing layer contains at least one further pharmaceutically acceptable excipient. The at least one further pharmaceutically acceptable excipient can be a buffer substance, for example a phosphate buffer or a citrate buffer, $Na_2HPO_4$, $NaH_2PO_4$, trisodium citrate, an acidifying agent, for example hydrochloric acid or citric acid, and/or an acidity regulator, for example sodium hydroxide.

The phosphate buffer can be contained in an amount of up to approximately 4.5 wt % in the at least one active-compound-containing layer. According to an additional and/or alternative embodiment, $Na_2HPO_4$ can be contained in an amount of up to approximately 1.0 wt % in the at least one active-compound-containing layer. According to an additional and/or alternative embodiment, $NaH_2PO_4$ can be contained in an amount of up to approximately 3.5 wt % in the at least one active-compound-containing layer.

The citrate buffer can be contained in an amount of up to 11.7 wt % in the at least one active-compound-containing layer. According to an additional and/or alternative embodiment, trisodium citrate can be contained in an amount of up to approximately 8.7 wt % in the at least one active-compound-containing layer. According to an additional and/or alternative embodiment, citric acid can be contained in an amount of up to approximately 3.0 wt % in the at least one active-compound-containing layer. According to an additional and/or alternative embodiment, trisodium citrate is contained in an amount of approximately 5.8 wt % and/or citric acid is contained in an amount of approximately 3.0 wt % in the at least one active-compound-containing layer.

The acidity regulator can be contained in an amount of up to approximately 1.0 wt % in the at least one active-compound-containing layer.

According to an additional and/or alternative embodiment, the at least one active-compound-containing layer has the following composition:

| Component | Content (wt %) |
| --- | --- |
| Polymer | 50-74 |
| Plasticizer | 9-20 |
| Active compound | 5.9-20 |
| Enhancer | 0-20 |
| Stabilizer | 1.4-22.9 |
| Preservative | 0.1-0.2 |
| Dye | 0-2.0 |
| Buffer | 0-4.5 |
| Acidity regulator | 0-1 |
| Acidifying agent | 0-3 |
| Total: | 100 |

According to an additional and/or alternative embodiment, the film-like dosage form comprises a cover layer. The cover layer is arranged on one of the two surfaces of the active-compound-containing layer or the laminate of at least two active-compound-containing layers, and when the dosage form is correctly applied to the oral mucosa, faces toward the oral cavity.

The cover layer of the film-like dosage form is essentially free of the active compound and provides selective release of the at least one antidiabetic peptide onto the oral mucosa, as it prevents the release into the oral cavity of the active compound contained in the dosage. For this purpose, the cover layer is either insoluble in saliva or decomposes in saliva significantly more slowly than the active-compound-containing layer. Preferably, the cover layer is essentially impermeable to the active compound contained in the active-compound-containing layer or active-compound-containing layers.

According to an additional and/or alternative embodiment, the at least one cover layer comprises a content of a polymer, preferably a content of ethylcellulose, as polymer films composed of ethylcellulose are highly flexible. The content of the polymer, more particularly ethylcellulose, in the cover layer is at least 50 wt %, preferably at least 55 wt %, particularly preferably at least 60 wt %, and most particularly preferably at least 65 wt %, based on the total weight of the cover layer. The content of the polymer, more particularly an ethylcellulose, in the cover layer is at most 99 wt %, preferably at most 95 wt %, particularly preferably at most 94 wt %, and most particularly preferably at most 93.5 wt %, based on the total weight of the cover layer.

According to a particular embodiment, the ethylcellulose is an ethylcellulose with a viscosity in the range of 90 to 110 mPa·s (cP), measured with an Ubbelohde viscometer at 25° C. for a 5% solution in a solvent mixture of 80 vol % toluene and 20 vol % ethanol. Such ethylcelluloses are also referred to as ethylcellulose 100.

According to an additional and/or alternative embodiment, the cover layer comprises at least one plasticizer. The content of plasticizers in the cover layer is preferably at least 5 wt %, particularly preferably at least 10 wt %, and most particularly preferably at least 15 wt %, based on the total weight of the cover layer. The content of plasticizers in the cover layer is preferably not more than 34 wt %, particularly preferably not more than 30 wt %, and most particularly preferably not more than 20 wt %, based on the total weight of the cover layer.

The plasticizer in the cover layer can be selected from the group comprising medium-chain triglycerides, glycerol, and citric acid esters such as triethyl citrate. Medium-chain triglycerides are triglycerides comprising medium-chain fatty acids. The medium-chain fatty acids include fatty acids with carbon chains of 6 to 12 C atoms, for example caproic acid (C 6:0), caprylic acid (C 8:0), capric acid (C 10:0), and lauric acid (C 12:0).

According to an additional and/or alternative embodiment, the cover layer comprises a dye. The content of the dye in the cover layer is between approximately 0.5 wt % and approximately 2 wt %, preferably approximately 1 wt % or approximately 1.5 wt %, based on the total weight of the cover layer.

The dye can be selected from the group composed of titanium dioxide and iron oxide.

According to an additional and/or alternative embodiment, the cover layer and the at least one active-compound-containing layer are of different colors. This allows the patient to distinguish the active-compound-containing layer from the cover layer and to apply the film-like dosage form with the proper orientation, so that the cover layer does not lie against the oral mucosa, but faces the oral cavity.

According to the second aspect, the invention relates to a method for the production of the above-described film-like dosage forms.

According to an embodiment of the method, the film-like dosage forms are produced by dissolving or suspending the components of the active-compound-containing layer(s) in a solvent. The resulting viscous mass is applied to a flat carrier in a specified thickness using a suitable film applicator, for example a doctor blade. After this, the active compound layer obtained in this manner is dried.

The method comprises the following steps:
dissolving and/or suspending the components of the active-compound-containing layer in a solvent,
applying the solution or suspension to a carrier in a specified thickness; and subsequent drying.

According to an embodiment, the solvent for the active-compound-containing layer is selected from the group comprising ethanol, water, and mixtures of water and ethanol, more particularly a mixture of approximately 96 vol % ethanol and approximately 4 vol % water (96% ethanol). According to an additional embodiment, the mixture of water and ethanol has a volume ratio of 80% to 20% (water to ethanol). Surprisingly, it was possible by using the above-mentioned mixtures of water and ethanol to achieve better active compound permeation from the resulting film-like dosage form, based on insulin, than in use of water as a solvent.

According to a further embodiment, the carrier is a flat carrier, for example a plastic film, preferably a polyethylene terephthalate film, a prefabricated active-compound-containing layer, a prefabricated cover layer, a prefabricated laminate comprising at least one active-compound-containing layer, or a prefabricated laminate comprising a cover layer and at least one active-compound-containing layer.

According to an embodiment, drying is carried out at a temperature of not more than 80° C., preferably not more than 50° C., particularly preferably at a temperature of approximately 50° C. By means of drying, the solvent is removed from the layer. The relatively low drying temperature ensures that the antidiabetic peptide is not destroyed during drying.

According to an additional and/or alternative embodiment, at least one further active-compound-containing layer is applied to an already-dried active compound layer by
dissolving and/or suspending the components of the further active-compound-containing layer in a solvent,
applying the solution or suspension to the dried active compound layer in a specified thickness, and
drying the further active compound layer obtained in this manner. The dried active compound layer to which the solution or suspension for the further active compound layer is applied therefore constitutes the flat carrier.

Preferably, the same solvent is used for the production of the further active-compound-containing layer(s) as for the production of the first active-compound-containing layer.

Preferably, drying of the further active-compound-containing layer(s) is carried out at a temperature of not more than 80° C., preferably not more than 50° C., particularly preferably at a temperature of approximately 50° C.

According to a further and/or alternative embodiment for the production of film-like dosage forms according to the present invention that have a cover layer, the components of the cover layer are dissolved or suspended in a solvent. The viscous mass obtained in this manner is applied using a suitable film applicator, for example a doctor blade, to the last dried active compound layer as a flat carrier and also dried.

In this embodiment, the method for production of the film-like dosage form comprises dissolving and/or suspending the components of the cover layer in a solvent, applying the solution or suspension for the cover layer to the last dried active compound layer, and drying the cover layer.

According to an embodiment, the solvent for the cover layer is selected from the group comprising water and mixtures of water and ethanol. According to an additional embodiment, the mixture of water and ethanol has a volume ratio of 80% to 20% (water to ethanol). According to an alternative embodiment, the solvent for the cover layer is ethanol (96%).

According to an embodiment, the cover layer is dried at a temperature of not more than 80° C., preferably not more than 50° C., particularly preferably at approximately 50° C. The drying removes the solvent from the layer. The relatively low drying temperature ensures that the antidiabetic peptide is not destroyed during drying.

According to an alternative embodiment for the production of film-like dosage forms according to the present invention that have a cover layer, the cover layer is first produced by applying a solution or suspension of the components of the cover layer to a flat carrier, preferably a plastic film, particularly preferably a polyethylene terephthalate film, in a specified thickness and then drying the material layer obtained in this manner. After this, at least one active-compound-containing layer is applied to the prefabricated cover layer as a carrier for the active-compound-containing layer in a specified thickness and dried.

For this production variant, the components of the cover layer are dissolved or suspended in a solvent, preferably in water, ethanol, or a mixture of water and ethanol, more particularly a mixture of 80 vol % water and 20 vol % ethanol, or ethanol (96%). The viscous mass obtained in this manner is applied with a suitable device, for example a doctor blade, to a carrier, preferably a plastic film, for example a polyethylene terephthalate film, in a specified thickness. The material layer obtained in this manner is dried, preferably as described above. Because no active compound can be adversely affected during this drying by the elevated drying temperature, it is also possible to dry the material layer for the cover layer at higher temperatures. This allows the drying time to be shortened and the production process as a whole to be accelerated.

After drying, an active-compound-containing layer is applied to the prefabricated cover layer. For this purpose, the components of the active-compound-containing layer are dissolved or suspended in a solvent, preferably in water, ethanol or a mixture of water and ethanol, more particularly a mixture of 80 vol % water and 20 vol % ethanol, or ethanol (96%). The resulting viscous active-compound-containing mass is applied with a suitable film applicator, for example a doctor blade, to the free surface of the prefabricated cover layer in a specified thickness.

After this, the active compound layer obtained in this manner is dried. According to an embodiment, drying is carried out at a temperature of not more than 80° C., preferably not more than 50° C., particularly preferably at approximately 50° C.

The method according to this embodiment thus comprises the following steps: dissolving and/or suspending the components of the cover layer in a solvent;

applying the solution to a flat carrier in a specified thickness;
drying of the cover layer;
dissolving or suspending the components of the active-compound-containing layer in a solvent;
applying the active-compound-containing solution to the prefabricated cover layer; and drying the active compound layer obtained in this manner.

Production of a film-like dosage form for the delivery of an antidiabetic peptide by prefabrication of the cover layer and subsequent application of the at least one active-compound-containing layer is less damaging to the active compound, because the antidiabetic peptide only has to be subjected to one drying phase, and further impairment of the active compound due to drying of the cover layer can be avoided. This production method, which is less damaging to the active compound, is advantageous because the efficacy of the active compound in the dosage form is affected to the least possible degree.

In a further embodiment, at least one further active-compound-containing layer can be applied to the active compound layer, which has already been dried and applied to the prefabricated cover layer, preferably in the manner described above for the active compound layer and/or the at least one further active compound layer.

According to a further embodiment of the production method, the dosage forms are separated from the active-compound-containing film or the resulting active-compound-containing laminate, comprising a plurality of active-compound-containing layers or at least one active-compound-containing layer and the cover layer, for example by cutting or punching. The separated dosage forms are then packaged, preferably individually packaged.

According to another embodiment of the production method, the active-compound-containing film or the resulting laminate, comprising a plurality of active-compound-containing layers or at least one active-compound-containing layer and the cover layer, can be cut into one or a plurality of strips of predetermined width and length. The active-compound-containing strips obtained in this manner are packaged as rolled or leporello-folded material. This type of packaging is advantageous in that depending on his or her individual requirements, a patient can cut off a section of the active-compound-containing strips containing the required amount of the active compound so that he or she can use the dosage form separated in this manner to deliver a suitable amount of the active compound tailored to his or her individual needs.

According to an additional embodiment, the strips of predetermined length have markings that indicate a predetermined amount of the active compound in the active-compound-containing strips. Preferably, the markings on the active-compound-containing strips are arranged at equal distances from one another. The markings can be lines, patterns, perforations, surface structures, notches, weakened areas or the like. Such markings make it easy for the user to precisely dose the active compound by detaching a section containing the desired amount of the active compound.

According to an additional and/or alternative embodiment, the active-compound-containing strips are packaged in a dispenser. Packaging of the active-compound-containing strips in a dispenser is advantageous because the active-compound-containing strips in this embodiment are thus immediately available for use by a patient, and the active-compound-containing strips themselves require no handling (unpacking, filling of a dispenser, etc.) by the patient and are nevertheless in a form that allows particularly user-friendly use, for example because the dispenser allows particularly precise dosing and/or particularly easy separation of the desired section.

Alternatively, the active-compound-containing strips can also be packaged individually rather than in a dispenser. In this configuration, the individually packaged active-compound-containing strips can be used as a refill package for a corresponding dispenser.

According to the third aspect, the invention relates to use of the above-described film-like dosage forms for the transmucosal delivery of an antidiabetic peptide, more particularly for delivery at least via one oral mucosa. The invention thus also pertains to a method for the delivery of at least one antidiabetic peptide via the oral mucosa, as well as to methods for the treatment of patients who require the delivery of an antidiabetic peptide.

According to a preferred embodiment of use of the film-like dosage form, the method for the delivery of at least one antidiabetic peptide, or use of the method for the treatment of a patient requiring the delivery of an antidiabetic peptide by means of the film-like dosage form, delivery of the film-like dosage form takes place on the mucosa of the gums (gingival application). Surprisingly, this application site for the dosage forms according to the invention has been found to be particularly favorable, more particularly with respect to the permeation of the antidiabetic peptide via the mucosa.

According to an embodiment, the film-like dosage form comprises insulin or an insulin analog as an active compound and is used for the treatment of diabetes mellitus type 1 or diabetes mellitus type 2.

Transmucosal delivery, more particularly the oral delivery and subsequent absorption of the antidiabetic peptide via the oral mucosa, is particularly comfortable for the user. The active compound diffuses directly through the mucosa into the bloodstream, thus generally allowing "first pass" metabolism to be avoided. This delivery method is easy to carry out and thus also suitable for patients with a visual disability and/or limited coordination capacity.

The invention is illustrated in the following use examples and with reference to the figures.

Here, neither the examples nor the figures limit the scope of the claimed invention, but are only for explanatory purposes.

Example 1

The components of the active-compound-containing layer were dissolved in water mixed with 0.141 wt % of 37% hydrochloric acid and applied with a film applicator to a polyethylene terephthalate film. The active compound layer was then dried at a temperature of 80° C.

After this, a further active compound layer was applied to the above-described active-compound-containing layer with the film applicator. The laminate was then dried at a temperature of 80° C. Individual doses measuring 4.11 cm$^2$ were then punched from the resulting film.

| Component | content in wt % |
|---|---|
| Hydroxypropylmethylcellulose, 100 USP | 54.000 |
| Hydroxypropylmethylcellulose, 4000 USP | 6.000 |
| Medium-chain triglycerides | 6.000 |
| Glycerol Ph. Eur./USP | 4.500 |
| Insulin | 5.925 |
| Na$_2$HPO$_4$ | 0.970 |

-continued

| Component | content in wt % |
|---|---|
| Na$_2$HPO$_4$, anhydrous | 3.500 |
| β-cyclodextrin | 10.405 |
| Poloxamer 188 (block copolymer of ethylene oxide and propylene oxide with an average mean relative molecular weight of 7680 to 9510) | 5.000 |
| Polyoxyethylene (23) lauryl ether | 1.500 |
| Disodium edetate | 0.100 |
| Methyl-4-hydroxybenzoate | 0.100 |
| Titanium dioxide | 2.000 |
| Total: | 100.000 |

The permeation rates achieved in an in vitro permeation test according to example 9 with film-like dosage forms according to this example are indicated in FIG. 1 by the curve labeled with -■-.

Example 2

The components of the active-compound-containing layer were dissolved in a solvent mixture of 20 wt % ethanol and 80 wt % water, applied with a film applicator to a polyethylene terephthalate film, and then dried at a temperature of 50° C.

Composition of the active-compound-containing layer

| Component | content in wt % |
|---|---|
| Hydroxypropylmethylcellulose, 100 USP | 34.424 |
| Hydroxypropylmethylcellulose, 4000 USP | 5.280 |
| Hydroxypropylmethylcellulose, 3 mPas | 22.000 |
| Triethyl citrate | 5.280 |
| Glycerol Ph. Eur./USP | 5.280 |
| Insulin | 12.000 |
| Na$_2$HPO$_4$, anhydrous | 2.640 |
| β-cyclodextrin | 4.998 |
| Poloxamer 188 (block copolymer of ethylene oxide and propylene oxide with an average mean relative molecular weight of 7680 to 9510) | 5.500 |
| Polyoxyethylene (23) lauryl ether | 1.601 |
| Disodium edetate | 0.320 |
| Methyl-4-hydroxybenzoate | 0.114 |
| Hydrochloric acid, 37% | 0.563 |
| Total: | 100.000 |

The components of the cover layer were dissolved in ethanol (96%) and applied with a film applicator to the above-described active-compound-containing layer. The laminate was then dried at a temperature of 50° C.

In the resulting two-layer film, the dried cover layer had a basis weight of 48.0 g/m$^2$, and the active-compound-containing layer had a basis weight of 114 g/m$^2$. Individual doses measuring 4.11 cm$^2$ were punched from the film.

Composition of the cover layer

| Component | content in wt % |
|---|---|
| Ethylcellulose 100 | 93.500 |
| Triethyl citrate | 5.000 |
| Iron oxide, yellow | 1.500 |
| Total | 100.000 |

The permeation rates achieved in an in vitro permeation test according to example 9 with film-like dosage forms according to this example are indicated in FIG. 1 by the curve labeled with -●-.

Example 3

The components of the active-compound-containing layer were dissolved in a solvent mixture of 20 wt % ethanol and 80 wt % water, applied with a film applicator to a polyethylene terephthalate film, and then dried at a temperature of 50° C.

Composition of the active-compound-containing layer

| Component | content in wt % |
| --- | --- |
| Hydroxypropylmethylcellulose, 100 USP | 34.050 |
| Hydroxypropylmethylcellulose, 4000 USP | 5.220 |
| Hydroxypropylmethylcellulose, 3 mPas | 21.240 |
| Triethyl citrate | 5.200 |
| Glycerol Ph. Eur./USP | 5.200 |
| Insulin aspart | 12.000 |
| $Na_2HPO_4$, anhydrous | 2.640 |
| Isopropyl myristate | 1.000 |
| Soy lecithin | 4.000 |
| Trehalose | 1.500 |
| β-cyclodextrin | 1.500 |
| Poloxamer 188 (block copolymer of ethylene oxide and propylene oxide with an average mean relative molecular weight of 7680 to 9510) | 4.500 |
| Polyoxyethylene (23) lauryl ether | 1.500 |
| Disodium edetate | 0.350 |
| Methyl-4-hydroxybenzoate | 0.100 |
| Total: | 100.000 |

The components of the cover layer were dissolved in ethanol (96%) and applied with a film applicator to the above-described active-compound-containing layer. The laminate was then dried at a temperature of 50° C.

In the resulting two-layer film, the dried cover layer had a basis weight of 48.0 g/m², and the active-compound-containing layer had a basis weight of 114 g/m². Individual doses measuring 4.11 cm² were punched from the film.

Composition of the Cover Layer

| Component | content in wt % |
| --- | --- |
| Ethylcellulose 100 | 93.500 |
| Triethyl citrate | 5.000 |
| Iron oxide, yellow | 1.500 |
| Total | 100.000 |

Figure 2:
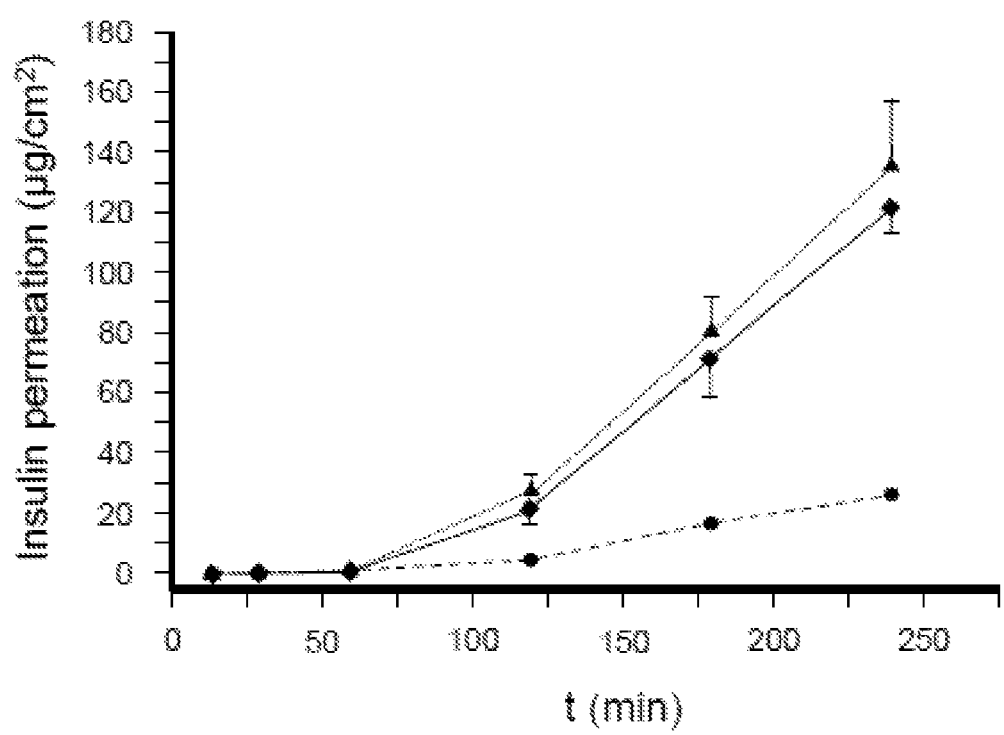
FIG. 2 shows a diagram illustrating the permeation of an insulin analog from three different film-like dosage forms in an in vitro permeation assay.

The permeation rates achieved in an in vitro permeation test according to example 9 with film-like dosage forms according to this example are indicated in FIG. 2 by the curve labeled with -●-.

Example 4

Composition of the Active-Compound-Containing Layer

| Component | content in wt % |
| --- | --- |
| Hydroxypropylmethylcellulose, 100 USP | 31.000 |
| Hydroxypropylmethylcellulose, 4000 USP | 4.800 |
| Hydroxypropylmethylcellulose, 3 mPas | 24.870 |
| Glycerol Ph. Eur./USP | 16.500 |
| Insulin aspart | 15.000 |
| Citric acid | 3.000 |
| Sodium hydroxide | 0.880 |
| Trehalose | 1.500 |
| β-cyclodextrin | 1.500 |
| Disodium edetate | 0.350 |
| Methyl-4-hydroxybenzoate | 0.100 |
| Titanium dioxide | 0.500 |
| Total: | 100.000 |

The components of the active-compound-containing layer were dissolved in a solvent mixture of 20 wt % ethanol and 80 wt % water, applied with a film applicator to a polyethylene terephthalate film, and then dried at a temperature of 50° C.

Composition of the cover layer:

| Component | content in wt % |
| --- | --- |
| Ethylcellulose 100 | 93.500 |
| Triethyl citrate | 5.000 |
| Iron oxide, yellow | 1.500 |
| Total | 100.000 |

The components of the cover layer were dissolved in ethanol (96%) and applied with a film applicator to the above-described active-compound-containing layer. The laminate was then dried at a temperature of 50° C.

In the resulting two-layer film, the dried cover layer had a basis weight of 48.0 g/m², and the active-compound-containing layer had a basis weight of 114 g/m². Individual doses measuring 4.11 cm² were punched from the film.

The permeation rates achieved in an in vitro permeation test according to example 9 with film-like dosage forms according to this example are indicated in FIG. 2 by the curve labeled with -♦-.

Example 5

The components of the active-compound-containing layer were dissolved in a solvent mixture of 20 wt % ethanol and 80 wt % water, applied with a film applicator to a polyethylene terephthalate film, and then dried at a temperature of 50° C.

Composition of the Active-Compound-Containing Layer

| Component | content in wt % |
| --- | --- |
| Hydroxypropylmethylcellulose, 100 USP | 31.000 |
| Hydroxypropylmethylcellulose, 4000 USP | 4.800 |
| Hydroxypropylmethylcellulose, 3 mPas | 20.070 |
| Glycerol Ph. Eur./USP | 16.500 |
| Insulin aspart | 15.000 |
| Citric acid | 3.000 |
| Sodium hydroxide | 0.880 |
| Trisodium citrate | 5.800 |
| Trehalose | 1.000 |
| β-cyclodextrin | 1.000 |
| Disodium edetate | 0.350 |
| Methyl-4-hydroxybenzoate | 0.100 |
| Titanium dioxide | 0.500 |
| Total: | 100.000 |

The components of the cover layer were dissolved in ethanol (96%) and applied with a film applicator to the above-described active-compound-containing layer. The laminate was then dried at a temperature of 50° C.

Composition of the Cover Layer

| Component | content in wt % |
|---|---|
| Ethylcellulose 100 | 93.500 |
| Triethyl citrate | 5.000 |
| Iron oxide, yellow | 1.500 |
| Total | 100.000 |

In the resulting two-layer film, the dried cover layer had a basis weight of 48.0 g/m², and the active-compound-containing layer had a basis weight of 114 g/m². Individual doses measuring 4.11 cm² were punched from the film.

The permeation rates achieved in an in vitro permeation test according to example 9 with film-like dosage forms according to this example are indicated in FIG. 2 by the curve labeled with -▲-.

Example 6

The components of the cover layer were dissolved in ethanol (96%), applied with a film applicator to a polyethylene terephthalate film, and then dried at a temperature of 50° C.

Composition of the Cover Layer

| Component | content in wt % |
|---|---|
| Ethylcellulose 100 | 88.500 |
| Triethyl citrate | 5.000 |
| Hydroxypropylmethylcellulose 100 | 5.000 |
| Iron oxide, yellow | 1.500 |
| Total | 100.000 |

The components of the active-compound-containing layer were dissolved in a solvent mixture of 20 wt % ethanol and 80 wt % water, applied with a film applicator to a polyethylene terephthalate film, and then dried at a temperature of 50° C.

Composition of the Active-Compound-Containing Layer

| Component | content in wt % |
|---|---|
| Hydroxypropylmethylcellulose, 100 USP | 29.250 |
| Hydroxypropylmethylcellulose, 4000 USP | 4.000 |
| Hydroxypropylmethylcellulose, 3 mPas | 18.000 |
| glycerol, anhydrous Ph. Eur./USP | 16.000 |
| Insulin aspart | 20.000 |
| Citric acid | 3.000 |
| Sodium hydroxide | 0.880 |
| Trisodium citrate | 5.800 |
| Trehalose | 1.000 |
| β-cyclodextrin | 1.000 |
| Disodium edetate | 0.470 |
| Methyl-4-hydroxybenzoate | 0.100 |
| Titanium dioxide | 0.500 |
| Total: | 100.000 |

In the resulting two-layer film, the dried cover layer had a basis weight of 48.0 g/m², and the active-compound-containing layer had a basis weight of 114 g/m². Individual doses measuring 4.11 cm² were punched from the film.

Figure 3:
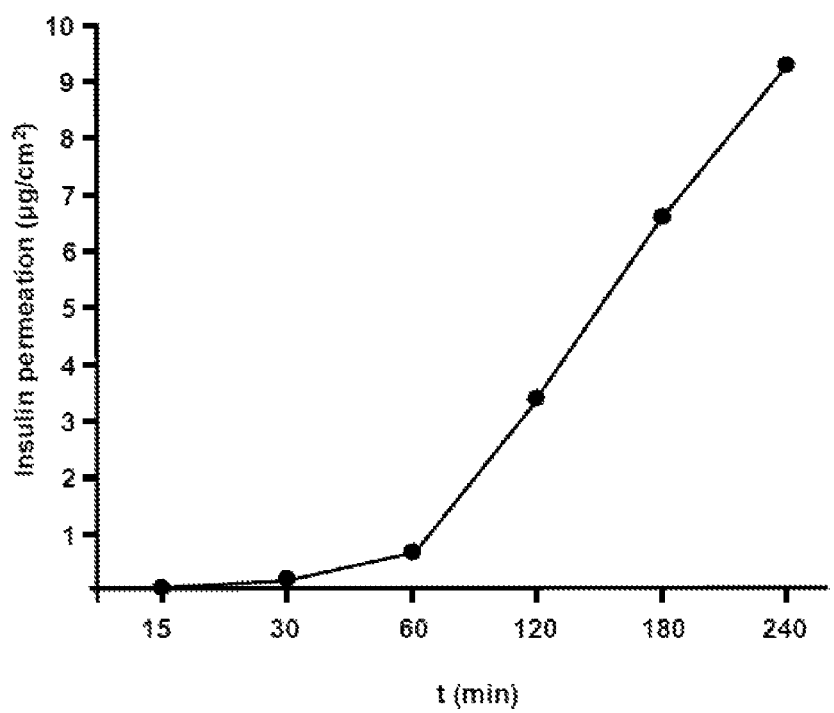
FIG. 3 shows a diagram illustrating the permeation of an insulin analog from one film-like dosage form in an in vitro permeation assay.

The permeation rates achieved in an in vitro permeation test according to example 9 with film-like dosage forms according to this example are shown in FIG. 3.

Example 7

The components of the cover layer were dissolved in ethanol (96%) and applied with a film applicator to the above-described active-compound-containing layer. The laminate was then dried at a temperature of 50° C.

Composition of the Cover Layer

| Component | content in wt % |
|---|---|
| Ethylcellulose 100 | 93.500 |
| Triethyl citrate | 5.000 |
| Iron oxide, yellow | 1.500 |
| Total | 100.000 |

The components of the active-compound-containing layer were dissolved in a solvent mixture of 20 wt % ethanol and 80 wt % water, applied with a film applicator to a polyethylene terephthalate film, and then dried at a temperature of 50° C.

Composition of the Active-Compound-Containing Layer

| Component | content in wt % |
|---|---|
| Hydroxypropylmethylcellulose, 100 USP | 34.424 |
| Hydroxypropylmethylcellulose, 4000 USP | 5.280 |
| Hydroxypropylmethylcellulose, 3 mPas | 22.000 |
| Triethyl citrate | 5.280 |
| Glycerol Ph. Eur./USP | 5.280 |
| Insulin glulisine | 12.000 |
| $Na_2HPO_4$ | 2.640 |
| β-cyclodextrin | 4.998 |
| Poloxamer 188 | 5.500 |
| Polyoxyethylene lauryl ether | 1.601 |
| Disodium edetate | 0.320 |
| Methyl-4-hydroxybenzoate | 0.114 |
| Hydrochloric acid | 0.563 |
| Total: | 100.000 |

In the resulting two-layer film, the dried cover layer had a basis weight of 48.0 g/m², and the active-compound-containing layer had a basis weight of 114 g/m². Individual doses measuring 4.11 cm² were punched from the film.

Figure 4:
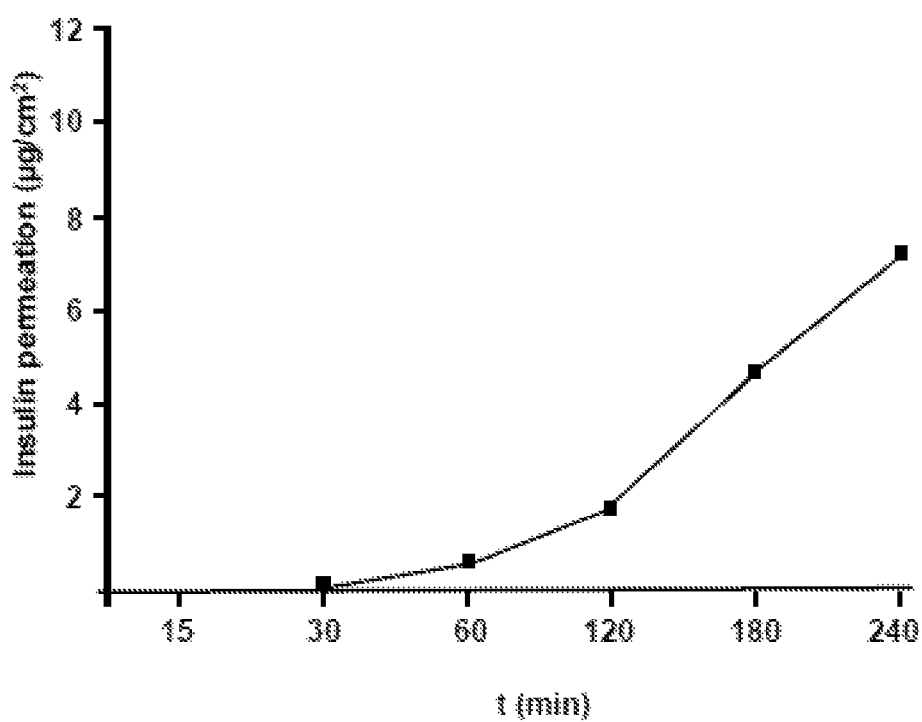
FIG. 4 shows a diagram illustrating the permeation of an insulin analog from one film-like dosage form in an in vitro permeation assay.

The permeation rates achieved in an in vitro permeation test according to example 9 with film-like dosage forms according to this example are shown in FIG. 4.

Example 8

The components of the cover layer were dissolved in ethanol (96%) and applied with a film applicator to the above-described active-compound-containing layer. The laminate was then dried at a temperature of 50° C.

Composition of the Cover Layer

| Component | content in wt % |
|---|---|
| Ethylcellulose 100 | 93.500 |
| Triethyl citrate | 5.000 |
| Iron oxide, yellow | 1.500 |
| Total | 100.000 |

The components of the active-compound-containing layer were dissolved in a solvent mixture of 20 wt % ethanol and 80 wt % water, applied with a film applicator to a polyethylene terephthalate film, and then dried at a temperature of 50° C.

In the resulting two-layer film, the dried cover layer had a basis weight of 48.0 g/m², and the active-compound-containing layer had a basis weight of 114 g/m². Individual doses measuring 4.11 cm² were punched from the film.

Composition of the Active-Compound-Containing Layer

| Component | content in wt % |
| --- | --- |
| Hydroxypropylmethylcellulose, 100 USP | 30.000 |
| Hydroxypropylmethylcellulose, 4000 USP | 4.500 |
| Hydroxypropylmethylcellulose, 3 mPas | 18.370 |
| Glycerol Ph. Eur./USP | 20.000 |
| Insulin lispro | 15.000 |
| Citric acid | 3.000 |
| Sodium hydroxide | 0.880 |
| Trisodium citrate | 5.800 |
| Trehalose | 1.000 |
| β-cyclodextrin | 1.000 |
| Disodium edetate | 0.350 |
| Methyl-4-hydroxybenzoate | 0.100 |
| Total: | 100.000 |

Figure 5:
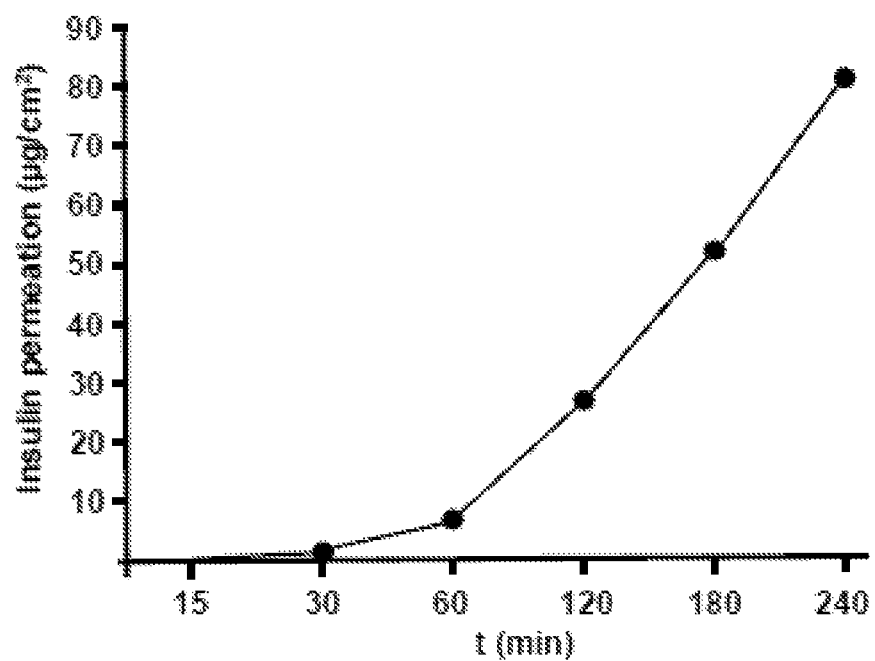
FIG. 5 shows a diagram illustrating the permeation of an insulin analog from one film-like dosage form in an in vitro permeation assay.

The permeation rates achieved in an in vitro permeation test according to example 6 with film-like dosage forms according to this example are shown in FIG. 5.

Example 9

Determination of the Permeation of Insulin Analogs In Vitro

The release and transmucosal permeation of insulin or insulin analogs was investigated in an in vitro model using the human epithelial skin model of the firm Skin Ethic, Lyon, FR. In this model, human keratinocytes of the cell line TR146 were cultivated on polycarbonate filters so that in a chemically defined medium, an epithelial tissue formed on the liquid interface with air that had no stratum corneum and thus at least histologically corresponded to the oral mucosa.

The individual polycarbonate filters containing the model tissue were placed in a diffusion chamber in order to separate the dispenser and acceptor compartments from each other, wherein the epithelium was oriented toward the lumen of the dispenser compartment. A film-like dosage form was applied to the epithelium, and the active compound in the acceptor compartment was determined at preset time intervals. The results for the preparations described in examples 1 through 4 are shown in FIGS. 1 and 2.

The invention claimed is:

1. A transmucosal film dosage form for the delivery of an antidiabetic peptide via the oral mucosa, comprising an active-compound-containing layer, said active-compound-containing layer comprising (i) at least one antidiabetic peptide and (ii) matrix polymer consisting of a mixture of at least two hydroxypropylmethylcelluloses of different viscosity within the active-compound-containing layer,
wherein the film dosage form residence time on the oral mucosa is from 30 minutes to 1 hour.

2. The film dosage form as claimed in claim 1, wherein the mixture of hydroxypropylmethylcelluloses is a mixture of a first hydroxypropylmethylcellulose, a second hydroxypropylmethylcellulose, and a third hydroxypropylmethylcellulose, in which the first hydroxypropylmethylcellulose is a hydroxypropylmethylcellulose of high viscosity, the second hydroxypropylmethylcellulose is a hydroxypropylmethylcellulose of medium viscosity, and the third hydroxypropylmethylcellulose is a hydroxypropylmethylcellulose of low viscosity.

3. The film dosage form as claimed in claim 2, wherein the hydroxypropylmethylcellulose of high viscosity has a viscosity of approximately 3,000 mPa·s to approximately 5,600 mPa, based upon a 2% solution in water at a temperature of 20° C. on a Brookfield LV viscometer.

4. The film dosage form as claimed in claim 3, wherein the hydroxypropylmethylcellulose of medium viscosity has a viscosity of approximately 75 mPa·s to approximately 140 mPa·s, based upon a 2% solution in water at a temperature of 20° C. on a Brookfield LV viscometer and
the film dosage form includes a single active-compound-containing layer.

5. The film dosage form as claimed in claim 2, wherein the hydroxypropylmethylcellulose of low viscosity has a viscosity of approximately 3 mPa·s, based upon a 2% solution in water at a temperature of 20° C. on a Brookfield LV viscometer.

6. The film dosage form as claimed in claim 1, wherein the at least one antidiabetic peptide is selected from the group consisting of insulins, insulin analogs, incretins, and incretin mimetics.

7. The film dosage form as claimed in claim 1, further having a cover layer.

8. The film dosage form as claimed in claim 7, wherein the cover layer comprises ethylcellulose and the ethylcellulose content in the cover layer is at least 50 wt %, but at most 99 wt %, based on the total weight of the cover layer.

9. A method for the production of the film dosage form for the transmucosal delivery of an antidiabetic peptide as claimed in claim 1, comprising the following steps:
dissolving and/or suspending components of the active-compound-containing layer in a solvent, thereby forming a solution or suspension,
applying the solution or suspension to a carrier in a specified thickness; and
subsequent drying.

10. The method as claimed in claim 9, further comprising
dissolving and/or suspending components of a cover layer in a solvent,
applying the solution or suspension for the cover layer to a carrier, and
subsequent drying of the cover layer.

11. The method as claimed in claim 10, wherein the solvent for dissolving or suspending the components of the active-compound-containing layer and/or the components of the cover layer is selected from the group comprising water and mixtures of water and ethanol.

12. The method as claimed in claim 9, wherein the drying is carried out at a temperature of not more than 80° C.

13. The method as claimed in claim 9, wherein the step of applying the solution or suspension with the components of the active-compound-containing layer is carried out on a prefabricated active-compound-containing layer or a prefabricated cover layer.

14. The method as claimed in claim 9, further comprising separating the film dosage form or cutting the film dosage form into strips of predetermined width and length; and subsequent packaging.

15. The film dosage form as claimed in claim 7, wherein the cover layer comprises ethylcellulose.

16. The film dosage form as claimed in claim 8, wherein the content of ethylcellulose in the cover layer is at least 55 wt %, but at most 95 wt %, based on the total weight of the cover layer.

17. The film dosage form as claimed in claim 8, wherein the content of ethylcellulose in the cover layer is at least 60 wt %, but at most 94 wt %, based on the total weight of the cover layer.

18. The film dosage form as claimed in claim 8, wherein the content of ethylcellulose in the cover layer is at least 65 wt %, but at most 93.5 wt %, based on the total weight of the cover layer.

19. The method as claimed in claim 11, wherein the solvent is a mixture of water and ethanol in a ratio of approximately 80 vol %:20 vol % or a mixture of water and ethanol in a ratio of approximately 4 vol %:96 vol %.

20. The method as claimed in claim 12, wherein the drying is carried out at a temperature of not more than 50° C.

21. A film dosage form for the delivery of an antidiabetic peptide via the oral mucosa, comprising an active-compound-containing layer, said active-compound-containing layer comprising (i) at least one antidiabetic peptide and (ii) matrix polymer consisting of a mixture of at least two hydroxypropylmethylcelluloses of different viscosity, wherein said mixture comprises a hydrodroxypropylmethylcellulose having a viscosity of approximately 3,000 mPa·s to approximately 5,600 mPa·s,
wherein the film dosage form residence time on the oral mucosa is from 30 minutes to 1 hour.

22. The film dosage form as claimed in claim 2, wherein the hydroxypropylmethylcelluloses are present in a weight ratio of 1:6 to 10:4.07 to 6 based on first hydroxypropylmethylcellulose:second hydroxypropylmethylcellulose:third hydroxypropylmethylcellulose.

23. The film dosage form as claimed in claim 1, wherein said film dosage form comprises permeability enhancer.

24. A transmucosal film dosage form for the delivery of an antidiabetic peptide comprising an active-compound-containing layer, said active-compound-containing layer comprising at least one antidiabetic peptide and matrix polymer consisting of a mixture of three hydroxypropylmethylcelluloses of different viscosities, wherein said film dosage form comprises at least 12 wt % antidiabetic peptide,
wherein the film dosage form residence time on the oral mucosa is from 30 minutes to 1 hour.

25. A transmucosal film dosage form as claimed in claim 24, wherein said film dosage form comprises at least 15 wt % antidiabetic peptide.

26. A transmucosal film dosage form for the delivery of an antidiabetic peptide via the oral mucosa, comprising at least one active-compound-containing layer, said at least one active-compound-containing layer comprising (i) at least one antidiabetic peptide and (ii) matrix polymer consisting of a mixture of three hydroxypropylmethylcelluloses of different viscosity within the active-compound-containing layer,
wherein the first hydroxypropylmethylcellulose has a viscosity of approximately 3,000 mPa·s to approximately 5,600 mPa·s, based upon a 2% solution in water at a temperature of 20° C. on a Brookfield LV viscometer
the second hydroxypropylmethylcellulose has a viscosity of approximately 75 mPa·s to approximately 140 mPa·s, based upon a 2% solution in water at a temperature of 20° C. on a Brookfield LV viscometer; and
the third hydroxypropylmethylcellulose has a viscosity of approximately 3 mPa·s, based upon a 2% solution in water at a temperature of 20° C. on a Brookfield LV viscometer, and
the at least one antidiabetic peptide is selected from the group consisting of insulins, insulin analogs, incretins, and incretin mimetics,
wherein the film dosage form residence time on the oral mucosa is from 30 minutes to 1 hour.

\* \* \* \* \*